United States Patent [19]

Nagasaki

[11] Patent Number: 4,748,985
[45] Date of Patent: Jun. 7, 1988

[54] ULTRASONIC IMAGING APPARATUS HAVING CIRCULATING COOLING LIQUID FOR COOLING ULTRASONIC TRANSDUCERS THEREOF

[75] Inventor: Tatsuo Nagasaki, Tokyo, Japan

[73] Assignee: Olympus Optical Co., Ltd., Tokyo, Japan

[21] Appl. No.: 858,950

[22] Filed: May 2, 1986

[30] Foreign Application Priority Data

May 10, 1985 [JP] Japan ................................ 60-99023

[51] Int. Cl.⁴ ............................................ A61B 10/00
[52] U.S. Cl. ........................................ 128/660; 128/4
[58] Field of Search ...................... 128/4, 6, 660, 661, 128/663; 73/623

[56] References Cited

U.S. PATENT DOCUMENTS

| | | | |
|---|---|---|---|
| 3,779,234 | 12/1973 | Eggleton et al. | 128/660 |
| 4,149,419 | 4/1979 | Connell, Jr. et al. | 128/660 X |
| 4,282,880 | 8/1981 | Gardineer et al. | 128/660 |
| 4,374,525 | 2/1983 | Baba . | |
| 4,375,818 | 3/1983 | Sawaki et al. | 128/660 |
| 4,391,282 | 7/1983 | Ando et al. | 128/660 |
| 4,432,236 | 2/1984 | Nagasaki . | |
| 4,633,882 | 1/1987 | Matsuo et al. | 128/660 |
| 4,674,515 | 6/1987 | Andou et al. | 128/660 |

OTHER PUBLICATIONS

Taylor, W. B. et al., "A High Resolution Transrectol UTS System", UTS in Medicine and Biology, pp. 129-138, (vol. 5 1979).

*Primary Examiner*—Francis J. Jaworski
*Attorney, Agent, or Firm*—Frishauf, Holtz, Goodman & Woodward

[57] ABSTRACT

An ultrasonic imaging apparatus comprises an ultrasonic transducer having two ultrasonic transducer elements which rotatably arranged back to back at the distal portion of an endoscope and a motor provided in the operation section of the endoscope and coupled to the transducer through a drive shaft to rotate the transducer. A transducer drover alternately drives the transducer elements during one rotation of the transducer. A switching circuit alternately switches the echo signals from the transducer elements during one rotation of the transducer. The echo signals of the transducer elements through the switch circuit are signal-processed and supplied to a TV monitor to display a tomographic image.

14 Claims, 2 Drawing Sheets

ULTRASONIC IMAGING APPARATUS HAVING CIRCULATING COOLING LIQUID FOR COOLING ULTRASONIC TRANSDUCERS THEREOF

BACKGROUND OF THE INVENTION

The present invention relates to a mechanical scanning type ultrasonic imaging apparatus and, more particularly, to an ultrasonic imaging apparatus which offers high scanning speed, improved transmission/reception S/N ratio, and improved resolution of a tomographic image.

Mechanical scanning type ultrasonic imaging apparatuses are widely used in the examination of living bodies. An endoscope/ultrasonic diagnostic apparatus combines such an ultrasonic imaging apparatus with an endoscope so as to perform diagnosis of an object to be examined. In such an endoscope/ultrasonic diagnostic apparatus, an ultrasonic transducer is rotatably mounted at the distal end of an endoscope and is driven through a drive shaft by a motor mounted at operation section of the endoscope. The endoscope scanning section has an angle sensor for detecting scanning angle. An ultrasonic wave reflected from an object, i.e., an echo, is converted into an electric echo signal by the ultrasonic transducer. The echo signal from the ultrasonic transducer is amplified by a preamplifier and output to an external lead through a mechanical contact, e.g., a brush. The echo signal at the lead is supplied to a display device and displayed as a tomographic image of the object. In order to increase tomographic image resolution, the frequency of a drive pulse can be increased. However, ultrasonic waves in the object attenuate in proportion to the square of the frequency. Detection sensitivity deteriorates abruptly upon such attenuation. In order to compensate for such sensitivity deterioration, the drive pulse is processed, e.g., pulse-compressed, to increase its level.

In the conventional ultrasonic imaging apparatus described above, a flexible shaft is used as a power transmission member for transmitting power to the transducer. When the transducer is driven at high speed, mechanical resonation occurs due to the mass of the transducer and the elasticity of the flexible shaft. Then, the transducer cannot be driven at a constant speed and irregularities occur during each rotation. Such irregular rotation results in flare or fogging, and thus poor image quality, in the resultant tomographic image. In order to prevent this, conventionally, the transducer is driven at low speed. However, the scanning speed drops at low transducer speeds, and an image of high quality cannot be easily obtained for objects with rapid movements such as a man's heart. In order to prevent the above-mentioned mechanical resonation, the rigidity of the flexible shaft can be increased. However, when a flexible shaft having a relatively high rigidity is used, the diameter of the endoscope insertion section is increased, and flexibility of the endoscope is impaired.

In a conventional ultrasonic imaging apparatus, the echo signal from the transducer is supplied to the display device through the brush as described above. Therefore, when the rotating speed of the transducer is increased, the brush vibrates, chattering increases, and the S/N ratio is lowered.

In order to increase resolution, the transmission output, i.e., the drive pulse, is increased in level by pulse compression. More heat is generated by the transducer because of its low conversion efficiency. The transducer can then be easily degraded and has a short life.

SUMMARY OF THE INVENTION

It is an object of the present invention to provide an endoscope/ultrasonic imaging apparatus which allows high speed scanning without causing flare or fogging of an image, which can obtain an excellent tomographic image of a rapidly moving object, which can provide an echo signal with high S/N ratio, and which can provide an object image with high resolution.

According to the present invention, two transducers are rotatably arranged back to back at the endoscope distal end with a damper medium interposed therebetween. The two transducer elements are switched upon each half rotation thereof for transmission/reception. A received signal or echo signal is supplied to a display device through a rotary transformer. The transducer elements are cooled by a circulating liquid filling a transducer housing and serving as an ultrasonic wave propagation medium.

DETAILED DESCRIPTION OF THE PREFERRED EMBODIMENT

Figure 1A:
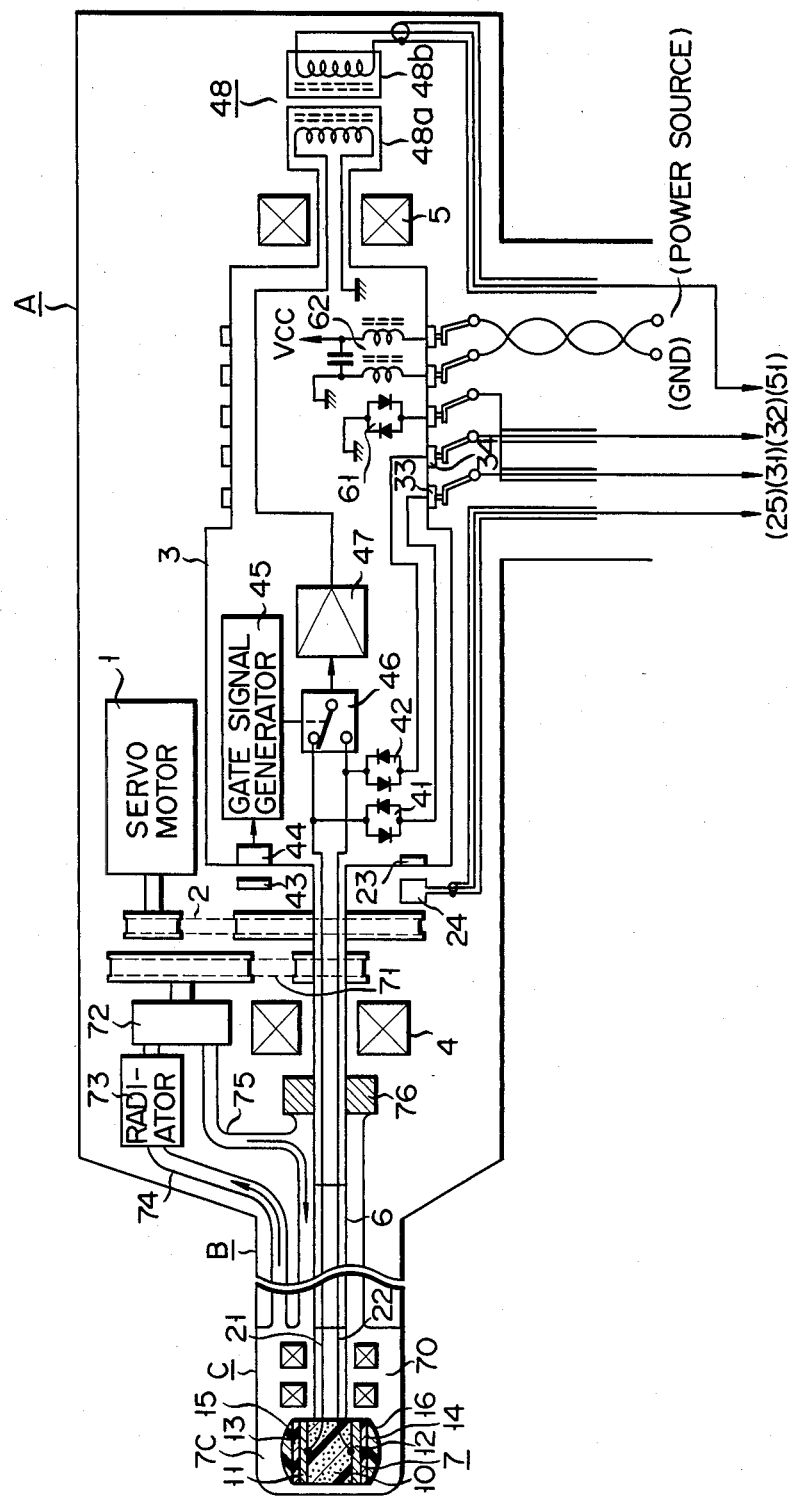
FIGS. 1A and 1B show a circuit diagram of an ultrasonic imaging apparatus according to an embodiment of the present invention.
Figure 1B:
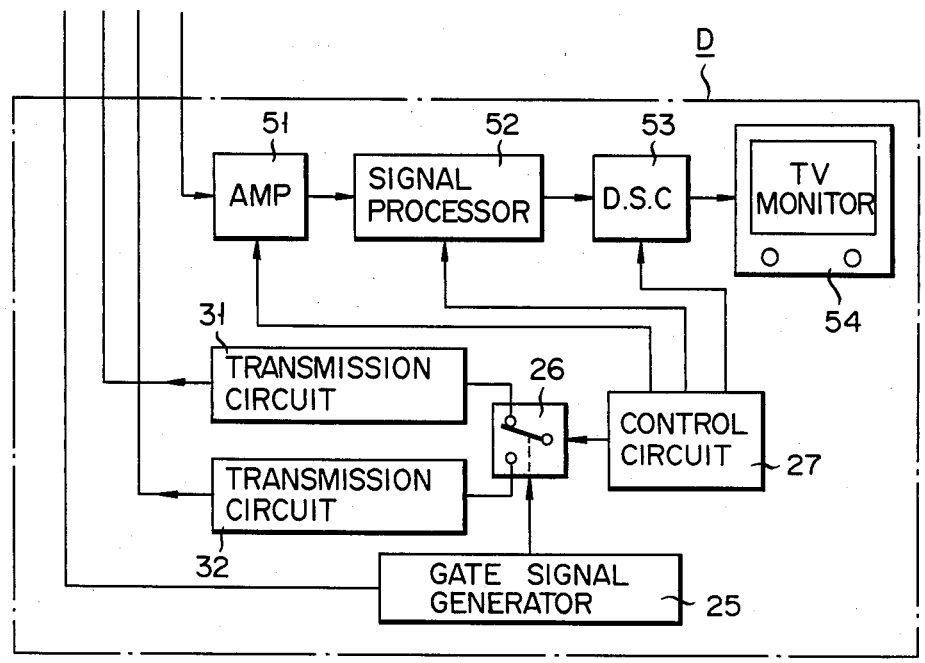

As seen in FIG. 1A, an endoscope comprises an operation section A, insertion section B extending from section A, and distal portion C at the distal end of section B.

Servo motor 1 is arranged in section A. Rotation of motor 1 is transmitted to rotary unit 3 by timing belt 2. Unit 3 is rotatably supported in section A by bearings 4 and 5. Motor 1, timing belt 2, and rotary unit 3 constitute a rotary driving unit.

Figures 2, 3:
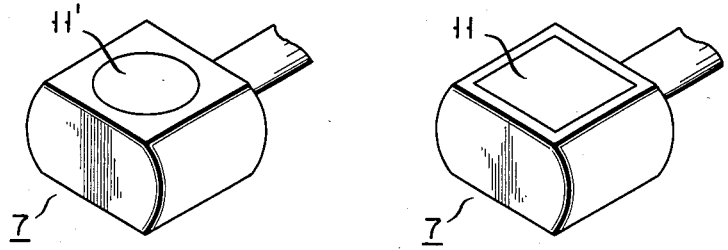
FIG. 2 is a perspective view of a transducer.
FIG. 3 is a perspective view of another transducer.

One end of unit 3 is coupled to hollow flexible shaft 6. Shaft 6 is rotatably inserted into section B. The distal end of shaft 6 extends into transducer housing 7C of portion C and is coupled to transducer rotor 7. Rotor 7 is rotatably housed in housing 7C and includes two transducer elements 11 and 12 fixed back to back with damper medium 10 interposed therebetween and formed of material absorbing ultrasonic waves. Elements 11 and 12 may be circular or square in shape as shown in FIGS. 2 and 3. When elements 11 and 12 are square, the opening area becomes 1.3 times that when elements 11 and 12 are circular, and the sensitivity and directivity of elements 11 and 12 are improved. Silicone convex lenses 15 and 16 are adhered to elements 11 and 12 through acoustic multi-layers 13 and 14 formed of material transmitting ultrasonic waves. Elements 11 and 12 are coupled to one end of each of signal cables 21 and 22 extending through shaft 6. Cables 21 and 22 extend into rotary unit 3 of section A.

A means for alternately outputting two sequences of drive signals for each half rotation of elements 11 and 12 is arranged in signal transmission/reception device D. The means has a photo-reflector 24 arranged to oppose mirror 23 mounted on an end face of unit 3. Photo-reflector 24 generates one sync pulse upon each half rotation of unit 3. When a sync pulse from photo-reflector 24 is supplied to gate signal generator 25 of control section D, generator 25 generates a gate pulse in synchronism with the received sync pulse. The gate pulse alternately switches switch 26. Therefore, a transmission trigger signal from control circuit (timing signal generator) 27 is alternately supplied to transmission circuits 31 and 32 through switch 26. Circuits 31 and 32 are alternately driven upon each half rotation of elements 11 and 12 and alternately supply two sequences of ultrasonic transmission signals to elements 11 and 12. A transmission signal from circuit 31 is supplied to unit 3 through rotary contact 33 in section A and then to element 11 through diode circuit 41 and signal cable 21. Similarly, a transmission signal from circuit 32 is supplied to element 12 through rotary contact 34, diode circuit 42, and signal cable 22. In this manner, elements 11 and 12 are energized upon each half rotation thereof.

An echo from an object is converted into echo signals by elements 11 and 12. The two sequences of echo signals are supplied to switch 46 through signal cables 21 and 22 and output from switch 46 as one echo signal sequence. More specifically, photo-reflector 44 mounted to oppose mirror 43 near an end face of unit 3 generates a pulse upon each half rotation of elements 11 and 12 in response to a signal output from photo-reflector 24. When the pulse from photo-reflector 44 is supplied to gate signal generator 45 of unit 3, generator 45 outputs a gate signal synchronous with the received pulse. Switch 46 alternately switches cables 21 and 22 in synchronism with the gate signal. Therefore, two echo signal sequences are alternately supplied to preamplifier 47 and output as one echo signal sequence from preamplifier 47.

The echo signal from preamplifier 47 is output to an external circuit from unit 3 through rotary transformer 48. The echo signal supplied to primary winding 48a of transformer 48 is transmitted to secondary winding 48b by electromagnetic induction. The echo signal from winding 48b is supplied to amplifier 51 of control section D. The echo signal from amplifier 51 is processed by signal processor 52 and supplied to digital scan converter 53. Converter 53 converts the input echo signal into a television signal and supplies it to TV monitor 54. TV monitor 54 thus displays a tomographic image.

Rotary unit 3 has diode circuit 61 for isolating the earth terminals of circuits 31 and 32 and preamplifier 47 from small signals. Diode circuit 61 thus serves to prevent introduction of contact noise and noise from the earth terminals. Unit 3 further has filter 62 for high-frequency separation of the power source and power source return power line in order to eliminate contact noise and power source noise.

Ultrasonic transmissive liquid 70 filling transducer housing 7C is circulated to remove heat generated by elements 11 and 12. For this purpose, motor 1 is coupled to circulation pump 72 (e.g., a peristaltic pump) through timing belt 2, drive shaft 6, and timing belt 71. The inlet and outlet ports of pump 72 communicate with housing 7C through radiator 73 and circulation paths 74 and 75 so as to allow circulation of liquid 70. Drive shaft 6 is shielded from liquid 70 by shielding member 76.

With the above apparatus, two transducer elements 11 and 12 are arranged back to back with damper medium 10 interposed therebetween. Elements 11 and 12 are rotated at the distal portion of section B and switched upon each half rotation thereof for reception of an echo. Therefore, even if the rotating speed of elements remains the same as in conventional apparatuses, the scanning speed is doubled.

Rotary transformer 48 extracts an echo signal outside unit 3. Therefore, even if the elements are driven at high speed, chattering noise such as is found in a conventional apparatus is not mixed in. Since the earth side of the signal in section A can be kept in the floating state, noise generated by motor 1 and the like is not mixed in. Since the liquid (water) used as an ultrasonic transmissive medium is circulated and cooled to cool elements 11 and 12, elements 11 and 12 can be driven by a high drive pulse obtained by pulse compression and can produce a high ultrasonic output. With such a high ultrasonic output, a tomographic image of high resolution can be obtained.

In the above embodiment, since the rotation angle is detected by two photo-reflectors 24 and 44, the number of rotary contacts in unit 3 can be reduced. In addition, since diode circuits 41 and 42 are provided, noise from circuits 31 and 32 and chattering noise can be prevented in the reception mode.

Diode circuit 61 and filter 62 serve to eliminate contact noise, earth noise, and power source noise.

In this manner, since the transmission output is high and noise is reduced, an object image does not contain flares or fog and an object under examination can be scanned at high speed. An image of a rapidly moving object such as a man's heart can therefore be obtained with high resolution and S/N ratio.

What is claimed is:

1. An endoscopic ultrasonic imaging apparatus comprising:
    an endoscope including an operation section and an insertion section extending from said operation section, said insertion section having a distal portion at a free end thereof remote from said operation section;
    transducer means having at least two ultrasonic transducer elements which are rotatably arranged in said distal portion of said endoscope, said transducer elements each having back surfaces which face inward towards each other, said transducer elements each emitting ultrasonic waves and converting echo waves into echo signals;
    housing means for housing said ultrasonic transducer means, said housing means being filled with ultrasonic transmissive cooling liquid;
    means defining a circulation path for said ultrasonic transmissive liquid contained in said housing means;
    means coupled to said circulation path for circulating said ultrasonic transmissive liquid in said circulation path and for cooling said ultrasonic transmissive liquid;
    rotating means arranged in said operation section of said endoscope and coupled to said transducer means for rotating said transducer means;
    drive shaft means, rotatably inserted in said insertion section of said endoscope, for coupling said transducer means and said rotating means;
    transducer drive means for alternately driving said at least two transducer elements during one rotation of said transducer means to alternately emit ultrasonic waves from said at least two transducer elements;
    said at least two transducer elements receiving echo signals reflected from bio-material during said rotation of said transducer means, and generating output echo signals responsive to received echo signals;

switching means for alternately switching said at least two transducer elements during one rotation of said transducer means to switch output echo signals produced by said transducer elements;

echo signal output means for outputting, as one echo signal sequence, output echo signals produced by said at least two transducer elements through said switching means;

signal processing means for signal-processing said echo signal sequence from said echo signal output means for converting it into a television signal; and display means for displaying the television signal from said signal procesing means as an image.

2. The apparatus of to claim 1, wherein:

said drive shaft means includes at least two signal cables inserted therein and connected respectively to said at least two transducer elements;

said operation section contains a rotary unit rotatably coupled thereto;

said rotary unit includes means for housing said switching means; and said switching means includes means for alternately switching said at least two signal cables.

3. The apparatus of claim 1, wherein said echo signal output means comprises a rotary transformer for transmitting said output echo signals through said switching means to said signal processing means by electromagnetic induction.

4. The apparatus of claim 1, wherein said transducer means comprises two ultrasonic transducer elements fixed together in back-to-back relationship, and a damper medium interposed between said backs of said two transducer elements, said damper medium being made of material absorbing ultrasonic waves.

5. The apparatus of to claim 4, wherein said ultrasonic transducer elements each have a substantially circular shape.

6. The apparatus of to claim 4, wherein said ultrasonic transducer elements each have a substantially square shape.

7. The apparatus of claim 4, wherein said ultrasonic transducer elements each have a substantially rectangular shape.

8. The apparatus of to claim 4, wherein said transducer means includes silicone convex lenses adhered to said ultrasonic transducer element, respectively.

9. The apparatus of claim 1, wherein said ultrasonic transducer elements each have a substantially circular shape.

10. The apparatus of claim 1, wherein said ultrasonic transducer elements each have a substantially square shape.

11. The apparatus of claim 1, wherein said ultrasonic transducer elements each have a substantially rectangular shape.

12. The apparatus of claim 1, wherein said transducer means includes silicone convex lenses adhered to said ultrasonic transducer elements, respectively.

13. The apparatus of claim 1, wherein:

said rotating means includes:

a servo motor;

a rotary unit rotated by said servo motor; and means for detecting the rotation of said rotary unit and for outputting a sync signal upon each half rotation of said rotary unit; and said transducer driving means includes means for alternately suppling a drive signal to said ultrasonic transducer elements in synchronism with said sync signal.

14. The apparatus of claim 1, wherein said circulating and cooling means includes:

a circulation pump; and a radiator; and said circulation path coupling together said circulation pump, said radiator and said housing to circulate said ultrasonic transmissive liquid.

* * * * *